United States Patent
Ladet et al.

(10) Patent No.: US 10,363,690 B2
(45) Date of Patent: Jul. 30, 2019

(54) METHOD FOR PREPARING A CHITOSAN-BASED POROUS LAYER

(71) Applicant: Sofradim Production, Trévoux (FR)

(72) Inventors: Sébastien Ladet, Caluire & Cuire (FR); Sebastien Francois, Jassans-Riottier (FR); Julien Claret, Villefranche sur Saone (FR); Maud Buffin, Lyons (FR)

(73) Assignee: Sofradim Production, Trévoux (FR)

( * ) Notice: Subject to any disclaimer, the term of this patent is extended or adjusted under 35 U.S.C. 154(b) by 873 days.

(21) Appl. No.: 14/413,499

(22) PCT Filed: Aug. 1, 2013

(86) PCT No.: PCT/EP2013/066238
§ 371 (c)(1),
(2) Date: Jan. 8, 2015

(87) PCT Pub. No.: WO2014/020132
PCT Pub. Date: Feb. 6, 2014

(65) Prior Publication Data
US 2015/0158209 A1    Jun. 11, 2015

(30) Foreign Application Priority Data
Aug. 2, 2012    (FR) ...................... 12 57551

(51) Int. Cl.
*B29C 43/02*    (2006.01)
*A61L 27/20*    (2006.01)
(Continued)

(52) U.S. Cl.
CPC ........ *B29C 43/02* (2013.01); *A61B 17/07292* (2013.01); *A61L 27/20* (2013.01);
(Continued)

(58) Field of Classification Search
CPC .......... A61L 27/20; A61L 27/50; A61L 27/56; B29C 43/02; A61B 17/07292;
(Continued)

(56) References Cited

U.S. PATENT DOCUMENTS 1,187,158 A    6/1916 Mcginley
3,054,406 A    9/1962 Usher
(Continued)

FOREIGN PATENT DOCUMENTS

AU    759066 B2 *    4/2003    ............. A61L 27/20
CA    1317836 C    5/1993
(Continued)

OTHER PUBLICATIONS

Wikipedia, Ammonium Hydroxide, 2012; https://en.wikipedia.org/wiki/Ammonia_solution.*
(Continued)

*Primary Examiner* — Anthony Calandra
*Assistant Examiner* — Jerzi H Moreno Hernandez (57) ABSTRACT

Method for preparing a chitosan-based porous layer The present invention relates to a method or preparing a chitosan-based, neutralized compressed porous layer, comprising the following steps: —a) a chitosan solution is prepared, —b) said solution is poured into a mold in order to form a layer, —c) the layer obtained in b) is lyophilized so as to obtain a porous layer, —d) said porous layer obtained in c) is compressed, —e) the compressed porous layer obtained in d) is neutralized by means of an $NH_4OH$ solution. It also relates to an implant comprising a layer obtained according to such a method.

20 Claims, 1 Drawing Sheet

(51) Int. Cl.
  *A61L 27/56* (2006.01)
  *A61B 17/072* (2006.01)
  *C08J 9/28* (2006.01)
  *C08L 5/08* (2006.01)
  *A61L 27/50* (2006.01)
  *B29L 7/00* (2006.01)

(52) U.S. Cl.
  CPC ............. *A61L 27/50* (2013.01); *A61L 27/56* (2013.01); *C08J 9/28* (2013.01); *C08L 5/08* (2013.01); *B29K 2005/00* (2013.01); *B29L 2007/00* (2013.01); *C08J 2201/0504* (2013.01); *C08J 2305/08* (2013.01)

(58) Field of Classification Search
  CPC .... B29K 2005/00; B29L 2007/00; C08J 9/28; C08J 2305/08; C08J 2201/0504; C08L 5/08
  See application file for complete search history.

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,525,710 A * | 6/1996 | Unger ............. B01J 20/26 536/18.7 |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |

(56) References Cited

U.S. PATENT DOCUMENTS

| | | |
|---|---|---|
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |

(56) References Cited

U.S. PATENT DOCUMENTS

| | | |
|---|---|---|
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0190346 A1* | 10/2003 | Lee ............. A61L 15/28 424/445 |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0021703 A1* | 1/2007 | McCarthy ............. A61L 15/28 602/43 |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0128932 A1* | 6/2008 | Hopman ............. A61F 13/00034 264/28 |
| 2008/0172071 A1 | 7/2008 | Barker |
| 2008/0242850 A1* | 10/2008 | Kim ............. A61L 15/28 536/20 |
| 2008/0255593 A1 | 10/2008 | St-Germain |
| 2009/0018479 A1* | 1/2009 | McCarthy ............. A61F 13/20 602/43 |
| 2009/0035341 A1 | 2/2009 | Wagener et al. |
| 2009/0036996 A1 | 2/2009 | Roeber |

(56) References Cited

U.S. PATENT DOCUMENTS

| | | | |
|---|---|---|---|
| 2009/0068250 A1 | 3/2009 | Gravagna et al. | |
| 2009/0105526 A1 | 4/2009 | Piroli Torelli et al. | |
| 2009/0163936 A1 | 6/2009 | Yang et al. | |
| 2009/0187197 A1 | 7/2009 | Roeber et al. | |
| 2009/0192530 A1 | 7/2009 | Adzich et al. | |
| 2009/0204129 A1 | 8/2009 | Fronio | |
| 2009/0216338 A1 | 8/2009 | Gingras et al. | |
| 2009/0270999 A1 | 10/2009 | Brown | |
| 2009/0281558 A1 | 11/2009 | Li | |
| 2009/0318752 A1 | 12/2009 | Evans et al. | |
| 2010/0082102 A1* | 4/2010 | Govil | A61L 27/54 623/11.11 |
| 2010/0104608 A1 | 4/2010 | Abuzaina et al. | |
| 2010/0318108 A1 | 12/2010 | Datta et al. | |
| 2011/0015760 A1 | 1/2011 | Kullas | |
| 2011/0144667 A1 | 6/2011 | Horton et al. | |
| 2011/0190795 A1 | 8/2011 | Hotter et al. | |
| 2011/0238094 A1 | 9/2011 | Thomas et al. | |
| 2011/0251699 A1* | 10/2011 | Ladet | A61L 31/044 623/23.72 |
| 2011/0257666 A1 | 10/2011 | Ladet et al. | |
| 2011/0311608 A1* | 12/2011 | Roorda | A61K 31/738 424/443 |
| 2011/0320009 A1* | 12/2011 | Ladet | A61L 27/48 623/23.72 |
| 2012/0016388 A1 | 1/2012 | Houard et al. | |
| 2012/0022242 A1* | 1/2012 | Domard | D01D 5/06 536/20 |
| 2012/0029537 A1 | 2/2012 | Mortarino | |
| 2012/0065727 A1 | 3/2012 | Reneker et al. | |
| 2012/0082712 A1 | 4/2012 | Stopek et al. | |
| 2012/0116425 A1 | 5/2012 | Intoccia et al. | |
| 2012/0150204 A1 | 6/2012 | Mortarino et al. | |
| 2012/0165937 A1 | 6/2012 | Montanari et al. | |
| 2012/0179175 A1 | 7/2012 | Hammell | |
| 2012/0179176 A1 | 7/2012 | Wilson et al. | |
| 2012/0197415 A1 | 8/2012 | Montanari et al. | |
| 2013/0164311 A1* | 6/2013 | DeCarlo | A61K 47/36 424/184.1 |
| 2014/0044861 A1 | 2/2014 | Boey et al. | |
| 2014/0364684 A1 | 12/2014 | Lecuivre | |

FOREIGN PATENT DOCUMENTS

| | | |
|---|---|---|
| CN | 201879864 U | 6/2011 |
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2 005 894 A2 | 12/2008 |
| EP | 2 008 595 A2 | 12/2008 |
| EP | 2229918 A1 | 9/2010 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| WO | 89/02445 A1 | 3/1989 |
| WO | 89/08467 A1 | 9/1989 |
| WO | 90/09769 A1 | 9/1990 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 9310731 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |

(56) References Cited

FOREIGN PATENT DOCUMENTS

| | | |
|---|---|---|
| WO | 01/15625 A1 | 3/2001 |
| WO | 01/80773 A1 | 11/2001 |
| WO | 01/81667 A1 | 11/2001 |
| WO | WO 01/92322 A1 | 12/2001 |
| WO | 02/007648 A1 | 1/2002 |
| WO | 0217853 A2 | 3/2002 |
| WO | 02/078568 A1 | 10/2002 |
| WO | WO 02/102276 A2 | 12/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | WO 2005/044285 A1 | 5/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2007/042281 A2 | 4/2007 |
| WO | 2007048099 A2 | 4/2007 |
| WO | 2009031035 A2 | 3/2009 |
| WO | 2009031047 A2 | 3/2009 |
| WO | 2009071998 A2 | 6/2009 |
| WO | WO 2009/111282 A2 | 9/2009 |
| WO | 2009156866 A2 | 12/2009 |
| WO | WO 2009/156866 A2 | 12/2009 |
| WO | WO 2010/042540 A1 | 4/2010 |
| WO | WO 2010/043978 A2 | 4/2010 |
| WO | 2011007062 A1 | 1/2011 |
| WO | 2011026987 A1 | 3/2011 |
| WO | 2011038740 A1 | 4/2011 |

OTHER PUBLICATIONS

Lu et al., Degradation of covalently cross-linked carboxymethyl chitosan and its potential application for peripheral nerve regeneration, 2007, European Polymer Journal, 43.9, pp. 3807-3818.*
International Written Opinion for PCT-EP2013-066238 dated Feb. 3, 2015 (Year: 2015).*
International Search Report for PCT/EP13/066238 date of completion is Oct. 24, 2013 (4 pages).
Doillon, C.J., et al., Collagen-based wound dressings: control of the pore structure and morphology, J. Biomed. Mater. Res., Oct. 1986, pp. 1219-1228, vol. 20(8).
Schoof, H. et al., Control of Pore Structure and Size in Freeze-Dried Collagen Sponges, Journal of Biomedical Materials Research, May 2001, pp. 352-357, vol. 58, No. 4.
European Office Action dated Mar. 31, 2017 in corresponding European Patent Application No. 13745399.9, 5 pages.
Ellouali, M. et al., "Antitumor Activity of Low Molecular Weight Fucans Extracted from Brown Seaweed Ascophyllum nodosum," Anticancer Res., Nov.-Dec. 1993, pp. 2011-2020, 12 (6A).
Malette, W. G. et al., "Chitosan, A New Hemostatic," Ann Th. Surg., Jul. 1983, pp. 55-58, 36.
Langenbech, M. R. et al., "Comparison of biomaterials in the early postoperative period," Surg Endosc., May 2003, pp. 1105-1109, 17 (7).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Klinge, U. et al., "Foreign Body Reaction to Meshes Used for the Repair of Abdominal Wall Hernias," Eur J. Surg, Sep. 1999, pp. 665-673, 165.
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Haneji, K. et al., "Fucoidan extracted from Cladosiphon Okamuranus Tokida Induces Apoptosis of Human T-cell Leukemia Virus Type 1-Infected T-cell Lines and Primary Adult T-Cell Leukemia Cells," Nutrition and Cancer, 2005, pp. 189-201, 52(2), published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.

(56) References Cited

OTHER PUBLICATIONS

Tolaimate, A., et al. "Contribution to the preparation of chitins and chitosans with controlled physico-chemical properties." Polymer, Dec. 2003, pp. 7939-7952, 44 (26).

O'Brien, F. J. et al., "Influence of freezing rate on pore structure in freeze-dried collagen-GAG scaffolds" Biomaterials, Mar. 2004, pp. 1077-1086, vol. 25, Issue 6.

Lamarque, G. et al., "Comparative Study of the Second and Third Heterogeneous Deacetylations of alpha- and beta-Chitins in a Multistep Process" Biomacromolecules, Sep.-Oct. 5, 2004, pp. 1899-1907, 5.

Lamarque, G. et al., Comparative Study of the First Heterogeneous Deacetylation of alpha- and beta-Chitins in a Multistep Process Biomacromolecules May-Jun. 2004, 992-1001, 5.

Lamarque, G. et al, "New Route of Deacetylation of alpha- and beta-Chitins by Means of Freeze-Pump Out-Thaw Cycles" Biomacromolecules, May-Jun. 2005, pp. 1380-1388, 6.

\* cited by examiner

METHOD FOR PREPARING A CHITOSAN-BASED POROUS LAYER

CROSS-REFERENCE TO RELATED APPLICATIONS

This application is a National Stage Application of PCT/EP13/066238 under 35 USC § 371 (a), which claims priority of French Patent Application Serial No. 12/57551 filed Aug. 2, 2012, the disclosures of each of the above-identified applications are hereby incorporated by reference in their entirety.

BACKGROUND

1. Technical Field

The present invention relates to a method for preparing a compressed porous layer of chitosan which has good mechanical strength, such a compressed porous layer being particularly useful for the manufacture of implants for reinforcing staple zones or lines, also called "buttresses".

2. Description of Related Art

Staple line reinforcing implants are used in particular in gastrointestinal surgery for reinforcing the zones requiring a plurality of sutures or staples, for instance staple lines for reinforcing an intestinal anastomosis. These implants then serve to reinforce these zones in order to prevent or at least reduce possible bleeding and the potential subsequent complications. These reinforcing implants must have very good mechanical properties, in particular good resistance to suturing, in other words a high tensile strength before breaking.

Chitosan is a polysaccharide which results from the deacetylation of chitin. Chitin is one of the most widespread natural polysaccharides on earth and is extracted from the exoskeletons of arthropods, from the endoskeletons of cephalopods and also from fungi.

Chitosan has properties, such as biodegradability, biore-sorbability, biocompatibility, non-toxicity and mechanical properties, which make it particularly advantageous for medical applications. Thus, chitosan can be incorporated into medical devices as a constituent of implants, for example in the form of sponges. Chitosan in fact offers a good compromise, given the desired properties, for a staple line reinforcing implant, namely good biological compatibility and good mechanical properties.

Moreover, staple line reinforcing implants, which may be permanent or biodegradable, must also have a good cell integration ability. Thus, these implants are often in the form of quite flat slabs formed from porous layers obtained from the lyophilization of a solution or solution of polymers.

Lyophilization involves a first step during which a solution is frozen in a particular structure, and then a second step, during which a controlled pressure is applied in order to cause sublimation of the water present in the frozen structure. At the end of the sublimation step, only the constituents present in the initial solution remain, thus producing a porous structure.

Once lyophilized, the chitosan-based porous layers are still very loaded with salts. These porous layers must therefore be neutralized and washed in order to remove these salts.

Moreover, the thickness of the implants for reinforcing staple zones or lines, or buttresses, is an important element of the effectiveness of the latter: indeed, this thickness must not be too great, so as, on the one hand, not to overload with foreign material the zones to be reinforced and, on the other hand, not to exceed the effectiveness-limiting height of the staples used; however, this thickness must not be too small either, so that the implant can perform its reinforcing role and the staple line can have a certain rigidity guaranteeing its durability, without damaging the biological tissue to be reinforced. Thus, the chitosan-based porous layers that it is desired to use as staple line reinforcements are generally compressed after lyophilization in order to attain a predetermined thickness. It is desirable to carry out this compression step before the neutralization step if it is desired for the deformation caused by the compression to be permanent and for the compressed layer not to reinflate in the presence of an aqueous medium such as biological fluids.

However, it has been observed that, when seeking to strongly compress chitosan-based porous layers, in particular when the chitosan concentration is high and the density of the resulting compressed layer is also high, the neutralization step is ineffective. In particular, such layers, although they have undergone a neutralization step, dissolve completely in the medium in which it is sought to wash them in order to eliminate any salts still remaining in these layers. These re-solubilizations result in the total destruction of the porous layer which can therefore no longer be used as a staple zone reinforcement.

It would be desirable to implement a method of preparing chitosan-based compressed porous layers that would avoid this phenomenon and would make it possible to effectively neutralize and wash such layers in order to prepare effective implants for reinforcing staple zones or lines, in particular buttresses.

SUMMARY

The present invention relates to a method for preparing a chitosan-based porous layer which has been compressed, neutralized and washed, comprising the following steps:
  a) a chitosan solution is prepared,
  b) said solution is poured into a mould in order to form a layer,
  c) the layer obtained in b) is lyophilized so as to obtain a porous layer,
  d) said porous layer obtained in c) is compressed,
  e) the compressed porous layer obtained in d) is neutralized by means of an $NH_4OH$ solution,
  f) the neutralized compressed porous layer obtained in e) is subjected to one or more washing steps.

BRIEF DESCRIPTION OF THE DRAWINGS

The invention and the advantages thereof will emerge more clearly from the examples below and from the appended figures, in which.

DETAILED DESCRIPTION

The method according to the invention makes it possible to obtain chitosan-based porous layers which have been compressed, neutralized and washed, containing a high concentration of chitosan. The term "chitosan-based" is intended to mean according to the present application that the major compound of the porous layer is chitosan. In particular, the compressed, neutralized and washed porous layers of chitosan obtained by means of the method according to the invention have a particularly high density. Thus, the porous layers obtained by means of the method according to the invention have excellent tensile strength and excellent resistance to suturing. They therefore make it possible to obtain particularly effective implants for reinforcing staple zones or lines.

According to a first step of the method according to the invention, step a), a chitosan solution is prepared.

Chitosan is a biocompatible biopolymer resulting from the deacetylation of chitin. Chitin is extracted from exoskeletons of arthropods such as lobster, crab or shrimp, from the endoskeleton of cephalopods such as squid, or else from fungi. The extraction of chitin involves steps of protein and lipid hydrolysis, of depigmentation and of demineralization. Usually, the protein and lipid hydrolysis is carried out in the presence of sodium hydroxide, the demineralization requiring the use of hydrochloric acid.

Once the chitin has been extracted, the chitosan is obtained by means of a deacetylation step, which consists of hydrolysis of the acetamide groups. This reaction is generally carried out at high temperature in an alkaline solution, for example a solution of sodium hydroxide (NaOH) at 48% in water, at 90° C.

The following publications also describe methods for deacetylation of chitin in order to obtain chitosan: "Lamarque, G., C. Viton, and A. Domard, *New Route of Deacetylation of α-and β-Chitins by Means of Freeze-Pump Out-Thaw Cycles*. Biomacromolecules, 2005. 6(3): p. 1380-1388.", "Lamarque, G., C. Viton, and A. Domard, *Comparative Study of the First Heterogeneous Deacetylation of α-and β-Chitins in a Multistep Process*. Biomacromolecules, 2004. 5(3): p. 992-1001.", "Lamarque, G., C. Viton, and A. Domard, *Comparative Study of the Second and Third Heterogeneous Deacetylations of α-and β-Chitins in a Multistep Process*. Biomacromolecules, 2004. 5(5): p. 1899-1907.", "Tolaimate, A., et al., *Contribution to the preparation of chitins and chitosans with controlled physicochemical properties*. Polymer, 2003. 44(26): p. 7939-7952."

Chitosans which are suitable as starting materials for the method according to the invention are available from the companies Kitozyme (fungus extract), Heppe Medical chitosan (shrimp or crab extract), Primex (shrimp extract) and Novamatrix (shrimp extract).

Chitosan is a biodegradable compound. The degree of acetylation of chitosan can have an influence on the chitosan degradation kinetics. Thus, depending on the biodegradation kinetics desired for the porous layer prepared according to the method of the invention, and therefore for the implant formed from this porous layer, the chitosan may have a degree of acetylation of 2, 3, 10, 20, 30, 40 or else 50%: the desired degree of acetylation can be obtained by preparing a mixture of several chitosans having various degrees of acetylation.

In one embodiment of the method according to the invention, the degree of acetylation of the chitosan ranges from 0 to 70%, preferably from 1% to 50%, preferably from 1% to 10% and more preferably from 2% to 3%. Such a chitosan makes it possible to obtain porous layers having optimum degradation kinetics and also a tissue growth substrate for the manufacture of staple line reinforcing implants.

The chitosan solution of step a) of the method according to the invention is generally prepared by solubilization of chitosan in powder form in water. The solution is adjusted to the desired pH, for example by adding acetic acid. In one embodiment of the method according to the invention, the pH of the chitosan solution is adjusted to a value ranging from 3 to 5, preferably to 3.5, for example by adding acetic acid. Such a pH makes it possible to obtain, in the end, a chitosan-based compressed porous layer which has good mechanical properties and which is capable of being stapled, for example.

In one embodiment of the method according to the invention, the solution of step a) is a solution of chitosan in water, the chitosan concentration in said solution ranging from 0.6% to 5%, preferably from 1% to 3% and more preferably from 2% to 3% by weight, relative to the total weight of the solution.

Such chitosan concentrations make it possible to obtain, in the end, compressed chitosan porous layers which have particularly good tensile strength and which are particularly resistant to suturing. Also preferably, the chitosan solution of the method according to the invention is free of any other polymer. The presence of a polymer other than chitosan in the solution could affect the lyophilization step and/or the compression step of the method according to the invention.

According to a second step of the method according to the invention, step b), the chitosan solution is poured into a mould in order to form a layer. Generally, the mould is in the shape of a rectangle having dimensions compatible with the use of the layer obtained as all or part of a reinforcing implant for staple zones in certain parts of the human body, for instance the gastrointestinal region.

According to a third step of the method according to the invention, step c), the layer obtained in b) is lyophilized so as to obtain a porous layer.

In the present application, the term "porous layer" is intended to mean a layer which has pores, or gaps, alveoli, holes, orifices, which are evenly or unevenly distributed not only at the surface, but also within the thickness of said layer, and which are more or less interconnected, depending on the lyophilization process used. Such lyophilization processes are known. It is known practice to vary the freezing temperature and speed and also the characteristics of the polymer solution to be lyophilized (pH, concentration, etc.), in this case chitosan, as a function of the structure of the sponge or porous layer that it is desired to obtain (see U.S. Pat. No. 4,970,298; Doillon et al, J Biomed Mater Res, 1986; Schoof, J Biomed Mater Res, 2001; O'Brien et al, Biomaterials, 2004).

According to a fourth step of the method according to the invention, step d), the porous layer obtained in c) is compressed. This compression can, for example, be carried out by means of a pneumatic press, such as a Mäder Pressen HP10000 HV10/50 press, Neuhausen, Germany.

The compression may be total, in other words it is carried out without inserting a wedge between the two jaws of the press used. In other embodiments of the method according to the invention, it is possible to insert a 2 mm wedge, or else a 1 mm wedge, in order to obtain a compressed layer respectively approximately 2 mm thick or 1 mm thick.

In one embodiment, the porous layer is compressed until a thickness of less than or equal to 2 mm, preferably less than or equal to 1 mm and more preferably less than or equal to 0.5 mm is obtained for said layer. This is because such thicknesses make it possible not to overload the staple zone that the reinforcing implant based on the porous layer obtained according to the invention will have to reinforce. In particular, this makes it possible not to exceed the load limiting height of the staples used and therefore to be able to use these staples effectively.

In particular, in one embodiment of the method according to the invention, said porous layer is compressed until a density of greater than or equal to 0.04 g/cm$^3$, preferably greater than or equal to 0.19 g/cm$^3$ and more preferably greater than or equal to 0.65 g/cm$^3$ is obtained for said layer. Such densities make it possible to obtain, in the end, porous layers which have particularly good tensile strength and which are particularly resistant to suturing.

According to a fifth step of the method according to the invention, step e), the compressed porous chitosan layer obtained in d) is neutralized by means of an NH$_4$OH solution.

In one embodiment of the method of the invention, the NH$_4$OH solution is a solution of NH$_4$OH in water or in ethanol, the NH$_4$OH concentration in said solution ranging from 0.6 to 2 mol/l. For example, the NH$_4$OH solution is a solution of NH$_4$OH in ethanol, the NH$_4$OH concentration in said solution ranging from 1 to 2 mol/l and preferably being 2 mol/l.

Such a solution allows effective neutralization of the compressed porous layers obtained in the previous step, both at the surface and at the heart of the layer, even if the layer has been strongly compressed, for example according to a total compression, and the layer has, after compression, a density greater than or equal to 0.20 g/cm$^3$. After the compression step described above, the porous layer can have a very fine thickness, for example less than or equal to 2 mm, or else less than or equal to 1 mm, or else less than or equal to 0.5 mm: moreover, it can have a high chitosan concentration, for instance that obtained using a starting chitosan solution of 1% to 3% by weight, relative to the total weight of the solution. The neutralization by means of an NH$_4$OH solution, in particular in water or in ethanol, the NH$_4$OH concentration in said solution ranging from 0.6 to 2 mol/l, preferably in ethanol, the NH$_4$OH concentration in said solution ranging from 1 to 2 mol/l and preferably being 2 mol/l, makes it possible to obtain deep neutralization of these high-density porous layers: in particular, the NH$_4$OH solution penetrates to the heart of the compressed porous layer.

In one embodiment of the method of the invention, the compressed porous layer obtained in d) is neutralized by dipping into said NH$_4$OH solution for a period of less than or equal to 30 min, preferably a period ranging from 5 min to 20 min. Such a period makes it possible to obtain a totally neutralized, compressed porous layer.

According to a sixth step of the method of the invention, step f), the neutralized compressed porous layer obtained in e) is subjected to one or more washing steps. The washing step makes it possible to eliminate from the porous layer any salts still remaining in this layer, for instance sodium acetate or ammonium acetate salts.

For example, the neutralized compressed porous layer is dipped in one or more baths of sterile water until a washing water with a pH close to 7 is obtained.

The porous chitosan layer which has been compressed, neutralized and washed according to the method of the invention can be part of or constitute the whole of an implant for reinforcing staple lines or zones. This is because these layers thus compressed, neutralized and washed have excellent tensile strength and excellent resistance to suturing.

Thus, another aspect of the invention relates to a chitosan-based porous layer which has been neutralized and washed, obtained from a layer obtained by lyophilization of a solution of chitosan in water, the chitosan concentration in said solution ranging from 0.6% to 5%, preferably from 1% to 3% and more preferably from 2% to 3% by weight, relative to the total weight of the solution, which layer has been compressed until a density of greater than or equal to 0.04 g/cm$^3$, preferably greater than or equal to 0.19 g/cm$^3$ and more preferably greater than or equal to 0.65 g/cm$^3$ has been obtained for said compressed layer.

When the chitosan solution used in the method of the invention is free of any other polymer, the chitosan-based porous layer obtained is also free of any other polymer. In embodiments, the chitosan-based porous layer is free of any other polymer.

EXAMPLE 1

Porous chitosan layers which have been compressed and neutralized are prepared according to the following protocols:

1°) Preparation of Chitosan Solutions at Different Chitosan Concentrations, and Having Different Weights:

15 g of chitosan with a 2% degree of acetylation (DA) was solubilized in 1344 ml of sterile water by adding 5.5 ml of acetic acid with stirring. The solution was brought from a pH of 5.11 to a pH of 3.5 by adding 39 ml of acetic acid. The solution was then diluted by adding 92 ml of sterile water in order to obtain a chitosan solution at 1% by weight, relative to the total weight of the solution (called 1% solution).

A part of this solution was used to prepare solution samples weighing, respectively, 60 g, 80 g and 100 g.

Another part of this 1% solution, namely 958.5 g, was diluted by adding 240 ml of sterile water and was adjusted to pH 3.5 by adding 0.5 ml of acetic acid. A solution of chitosan at 0.8% by weight, relative to the total weight of the solution (called 0.8% solution), is obtained. A part of this 0.8% solution is used to prepare solution samples weighing, respectively, 60 g, 80 g and 100 g.

Another part of the 0.8% solution, namely 680 g, is diluted by adding 227 ml of sterile water and is adjusted to pH 3.5 by adding 0.5 ml of acetic acid. A chitosan solution at 0.6% by weight, relative to the total weight of the solution (called 0.6% solution), is obtained. This 0.6% solution is used to prepare solution samples weighting, respectively, 60 g, 80 g and 100 g.

The various types of samples of solutions S1-S9 collated in Table I below are therefore obtained:

TABLE I

| Types of solution samples prepared | | |
|---|---|---|
| Sample of solution | Chitosan concentration (by weight) | Weight of the solution in g |
| S1 | 0.6% | 60 |
| S2 | 0.6% | 80 |
| S3 | 0.6% | 100 |
| S4 | 0.8% | 60 |
| S5 | 0.8% | 80 |
| S6 | 0.8% | 100 |
| S7 | 1% | 60 |
| S8 | 1% | 80 |
| S9 | 1% | 100 |

2°) Preparation of Compressed Porous Layers from the Solutions Obtained in 1°):

After centrifugation, all the samples of solutions prepared in 1°) were each poured into a rectangular mould with dimensions 12 cm×17 cm, and then lyophilized for 28 h.

The porous layers C1-C9 obtained, respectively, from the lyophilization of the solutions S1-S9 of point 1°) are thus obtained.

The porous layers C1-C9 are then each subjected to a compression according to the following protocol: each layer is compressed using a pneumatic press (Mäder Pressen HP10000 HV10/50, Neuhausen, Germany) fixed at 4 bar for a cycle of 13 seconds. A final load of 67 kN is applied during the cycle after 4 seconds and is maintained until the end of the cycle. This compression is carried out without wedges.

The compressed porous layers CC1-CC9, obtained, respectively, from the porous layers C1-C9 above, are thus obtained, said compressed porous layers having the following characteristics:

TABLE II

Thickness and density of the compressed porous layers

| Compressed porous layer | Thickness in mm | Density (g/cm³) |
|---|---|---|
| CC1 | 0.13 | 0.19 |
| CC2 | 0.14 | 0.24 |
| CC3 | 0.15 | 0.28 |
| CC4 | 0.13 | 0.25 |
| CC5 | 0.2 | 0.22 |
| CC6 | 0.2 | 0.28 |
| CC7 | 0.16 | 0.26 |
| CC8 | 0.21 | 0.26 |
| CC9 | 0.33 | 0.21 |

3°) Preparation of Compressed Porous Layers Neutralized with Ammonia (According to the Invention):

A part of the compressed porous layers CC1-CC9 obtained in 2°) are subjected to a neutralization step according to the following protocol: each layer is dipped in a solution of $NH_4OH$ at 1 mol/l in ethanol for 5 min for the purpose of eliminating the salts potentially remaining in the layer.

It is noted that the layers are effectively neutralized. They can then be washed in baths of sterile water, until a washing water with a pH close to 7 is obtained, without risk of re-solubilization.

These porous chitosan layers which have been compressed, neutralized and washed can be used effectively in staple line reinforcing implants. They have tensile strength and are resistant to suturing.)

4°) Preparation of Compressed Porous Layers Neutralized with Sodium Hydroxide (Comparative):

The other part of the compressed porous layers CC1-CC9 obtained in 2°) is subjected to a neutralization step according to the following protocol: each layer is dipped in a solution of NaOH at 0.5 mol/l in ethanol for 5 min, for the purpose of eliminating the salts potentially remaining in the layer.

It is noted that only the surface of the layer is neutralized. During the washes in the baths of sterile water which follow the neutralization step, it is noted that the compressed porous layer re-solubilizes and is therefore destroyed.

Thus, it is not possible to obtain porous layers which have been compressed, neutralized and washed, when the neutralization is carried out with sodium hydroxide.

EXAMPLE 2

Porous chitosan layers were prepared according to the following protocols:

1°) Preparation of Compressed Porous Chitosan Layers:

21 g of chitosan with a 3% degree of acetylation (DA) were solubilized in 2442 ml of sterile water by adding 8 ml of acetic acid with stirring. The solution was brought from a pH of 5.11 to a pH of 3.5 by adding 60 ml of acetic acid. The solution was then diluted by adding 94 ml of sterile water in order to obtain a chitosan solution at 0.8% by weight, relative to the total weight of the solution.

Samples of this solution were centrifuged and then each poured into a rectangular mould with dimensions of 12 cm×17 cm, and then lyophilized for 28 h.

The porous layers obtained by lyophilization were then compressed in the same way as in EXAMPLE 1.)

2°) Neutralization of the Compressed Porous Layers Obtained in 1°):

Six compressed porous layers obtained in 1°), namely the samples CC11-CC16, were neutralized, each according to a different protocol, detailed hereinafter:

CC11: the compressed porous layer was dipped in a solution of NaOH at 0.5 mol/l in ethanol for 20 min, CC12: the compressed porous layer was dipped in a solution of NaOH at 0.5 mol/l in sterile water for 20 min, CC13: the compressed porous layer was dipped in a solution of $NH_4OH$ at 1 mol/l in ethanol for 20 min, CC14: the compressed porous layer was dipped in a solution of $NH_4OH$ at 1 mol/l in sterile water for 20 min, CC15: the compressed porous layer was dipped in a solution of $NH_4OH$ at 1 mol/l in ethanol for 5 min, CC16: the compressed porous layer was dipped in a solution of $NH_4OH$ at 1 mol/l in sterile water for 5 min.

The compressed porous layers CC11-CC16 neutralized as described above were then washed twice in sterile water. Their quality was then evaluated visually in the following way:

Presence of bubbles, or deformation or shrinking: graded "poor",

Even surface and nondeformed flat layer: graded "good".

The results are collated in Table III below:

TABLE III

Visual appearance of compressed porous chitosan layers as a function of the neutralization carried out

| Sample | Neutralization | Visual appearance |
|---|---|---|
| CC11 | NaOH 0.5 mol/l ethanol, 20 min | Poor |
| CC12 | NaOH 0.5 mol/l sterile water, 20 min | Poor |
| CC13 | $NH_4OH$ 1 mol/l ethanol, 20 min | Good |
| CC14 | $NH_4OH$ 1 mol/l sterile water, 20 min | Good |
| CC15 | $NH_4OH$ 1 mol/l ethanol, 5 min | Good |
| CC16 | $NH_4OH$ 1 mol/l sterile water, 5 min | Good |

EXAMPLE 3

A chitosan solution at 2% by weight, relative to the total weight of the solution, and having a pH of 3.5, was prepared.

Samples of 121 g of this solution were centrifuged and then each poured into a rectangular mould with dimensions of 12 cm×17 cm, and then lyophilized for 28 h.

The porous layers obtained by lyophilization were then compressed in the same way as in EXAMPLE 1.

A part of the compressed porous chitosan layers thus obtained were neutralized by dipping in an $NH_4OH$ solution at 1 mol/l for 20 min: the neutralization was effective.

Another part of the compressed porous chitosan layers thus obtained was neutralized by dipping in a solution of $NH_4OH$ at 2 mol/l in ethanol for 5 min: the neutralization was effective.

EXAMPLE 4

According to the preparation method of EXAMPLE 1, chitosan solutions at pH 3.5 were prepared at respective concentrations of 1%, 2% and 3%, by weight, relative to the total weight of the solution. 121 g solution samples were then prepared. After centrifugation, these solution samples were each poured into a rectangular mould with dimensions of 12 cm×17 cm, and then lyophilized for 28 h.

Porous chitosan layers were thus obtained. For each initial chitosan concentration, samples of these porous layers were compressed, each according to one of the following three protocols:

Total Compression:

The layer is compressed using a pneumatic press (Mäder Pressen HP10000 HV10/50, Neuhausen, Germany) fixed at 6 bar for a cycle of 13 seconds. This compression is carried out without wedges.

2 mm Compression:

Corresponds to the protocol above for total compression, but a 2 mm wedge is inserted between the two jaws of the press.

1 mm Compression:

Corresponds to the protocol above for total compression, but a 1 mm wedge is inserted between the two jaws of the press.

The samples of compressed porous layers and the values of their respective density after compression are collated in Table IV below, in which:

for each type of sample, the value indicated corresponds to an average for two tests, C by weight: represents the chitosan concentration by weight, relative to the total weight of the starting solution, T1: represents the thickness of the porous layer after lyophilization and before compression, T2: represents the thickness of the porous layer after compression, D is the density in g/cm$^3$ of the porous layer after compression and before neutralization. The volume of the porous layer is known from the dimensions of the mould and from the thickness of the layer after compression. The weight of the layer is measured and its density is thus determined.

TABLE IV

Density of the compressed porous layers before neutralization

| Sample | C by weight | Compression | T1 (mm) | T2 (mm) | D (g/cm$^3$) |
| --- | --- | --- | --- | --- | --- |
| CC21 | 1% | total | 4.59 | 0.15 | 0.68 |
| CC22 | 1% | 2 mm | 4.08 | 2.10 | 0.04 |
| CC23 | 1% | 1 mm | 3.84 | 1.06 | 0.09 |
| CC24 | 2% | total | 4.92 | 0.27 | 0.75 |
| CC25 | 2% | 2 mm | 4.90 | 2.27 | 0.09 |
| CC26 | 2% | 1 mm | 4.88 | 1.14 | 0.18 |
| CC27 | 3% | total | 4.79 | 0.41 | 0.70 |
| CC28 | 3% | 2 mm | 4.63 | 2.28 | 0.12 |
| CC29 | 3% | 1 mm | 4.37 | 1.16 | 0.23 |

All the compressed porous layers obtained were neutralized by dipping in a solution of NH$_4$OH at 2 mol/l in ethanol for 20 min: the neutralization was then effective.

The neutralized layers were then washed in baths of sterile water until washing water with a pH close to 7 was obtained. No re-solubilization of the layers was noted during this washing step.

Thus, the method according to the invention makes it possible to neutralize and wash porous chitosan layers having particularly high densities, which can range up to 0.75 g/cm$^3$, for example having densities greater than or equal to 0.65 g/cm$^3$ (see CC21, CC27 and CC24). The method according to the invention also makes it possible to neutralize and wash porous chitosan layers of which the chitosan concentration is particularly high, in particular porous chitosan layers obtained from a starting solution containing 3% chitosan (see CC27-29).

Moreover, the final density (FD) of the above compressed porous layers after neutralization was calculated according to the following formula: W×C/VF, where W is the weight of the layer, C is the chitosan concentration by weight, relative to the total weight of the starting solution, and VF is the volume of the layer measured after neutralization. The results are set out in Table V below:

TABLE V

Final density of the compressed porous layers after neutralization

| Sample | FD (g/cm$^3$) |
| --- | --- |
| CC21 | 0.44 |
| CC22 | 0.05 |
| CC23 | 0.08 |
| CC24 | 0.29 |
| CC25 | 0.08 |
| CC26 | 0.12 |
| CC27 | 0.29 |
| CC28 | 0.11 |
| CC29 | 0.15 |

Figure 1:
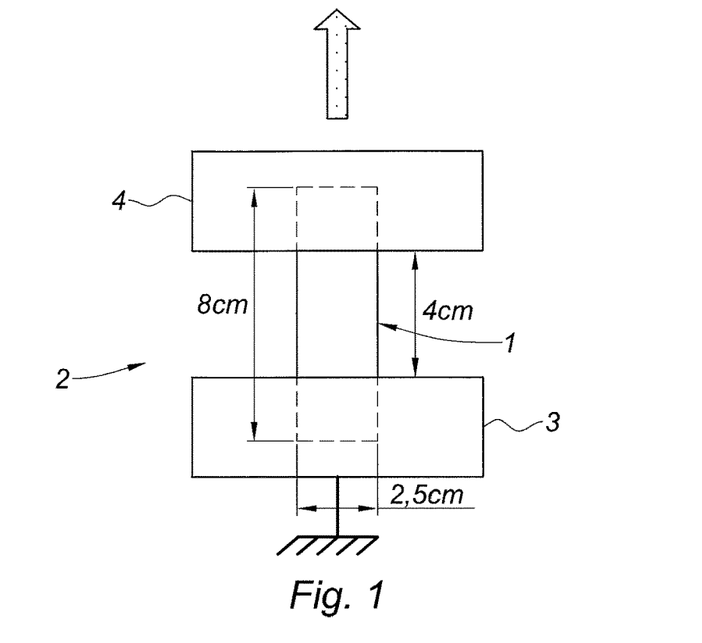
FIG. 1 is a diagram explaining how the tensile strength test works.

Tensile Strength Tests:

The tensile strength of the above compressed porous layers which have been neutralized and washed, CC21-29, was evaluated according to the following protocol: with reference to FIG. 1, for each layer CC21-29, a wet sample 1 of 8 cm×2.5 cm is mounted on a machine 2 equipped with a cell loaded at 100 N, comprising a fixed jaw 3 and a mobile jaw 4. Each end (over approximately 2 cm) of the sample 1 is fixed to a jaw (3, 4). A constant extension speed of 50 mm/min is then applied to the mobile jaw 4, and the force F necessary to achieve breaking of the sample 1 is measured.

The results are collated in Table VI below, in which the value of the force F corresponds to the mean for five tests.

TABLE VI

Tensile strength of the layers CC21-CC29

| Sample | CC21 | CC22 | CC23 | CC24 | CC25 | CC26 | CC27 | CC28 | CC29 |
| --- | --- | --- | --- | --- | --- | --- | --- | --- | --- |
| F (N) | 18.57 | 10.82 | 12.98 | 20.42 | 19.14 | 27.58 | 50.56 | 37.05 | 26.02 |

These results show that the tensile strength of the porous chitosan layers obtained according to the method of the invention is particularly high. These porous layers are thus entirely useful for the manufacture of implants for reinforcing staple zones or lines.

Figure 2:
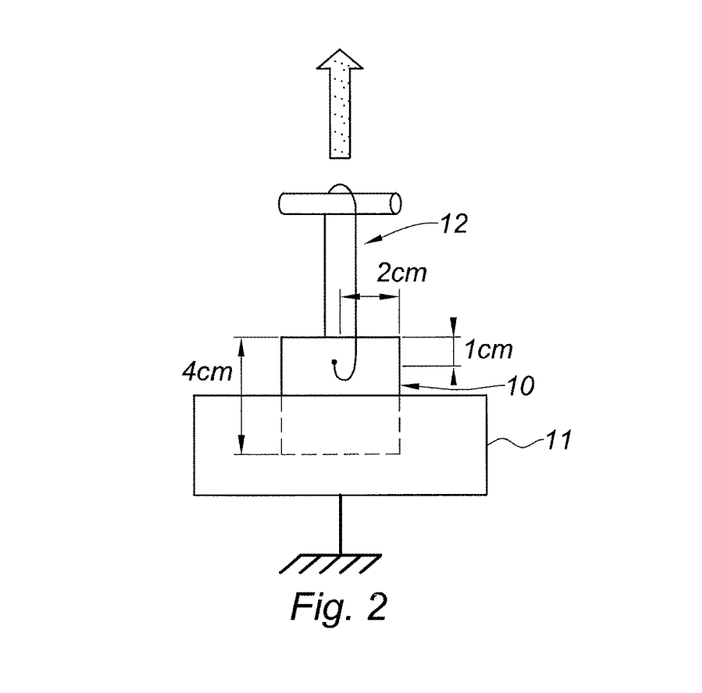
FIG. 2 is a diagram explaining how the suturing resistance test works.

Tests for Resistance to Suturing:

The resistance to suturing of the above compressed porous layers which have been neutralized and washed, CC21-29, was evaluated according to the following protocol: with reference to FIG. 2, for each layer CC21-29, a sample 10 of 4 cm×4 cm is attached, via one of its edges, to a fixed jaw 11. A suture thread 12 ("Surgipro II 5-0" commercially available from the company Covidien) is introduced at the centre of the sample 10, 1 cm from the edge. A constant extension speed of 50 mm/min is then applied to the suture thread 12, and the force F required to achieve breaking of the sample 10 is measured.

The results are collated in Table VII below, in which the value of the force F corresponds to the mean for five tests.

TABLE VII

Resistance to suturing of the layers CC21-CC29

| Sample | CC21 | CC22 | CC23 | CC24 | CC25 | CC26 | CC27 | CC28 | CC29 |
|---|---|---|---|---|---|---|---|---|---|
| F (N) | 1.773 | 1.471 | 1.227 | 3.172 | 2.536 | 3.434 | 3.020 | 3.920 | 2.418 |

These results show that the resistance to suturing of the porous chitosan layers obtained according to the method of the invention is particularly high. These porous layers are thus entirely useful for the manufacture of implants for reinforcing staple zones or lines.

What is claimed is:

1. A method for preparing a chitosan-based porous layer which has been compressed, neutralized and washed, comprising the following steps:
   a) preparing a chitosan solution free of any other polymer, including a chitosan concentration ranging from 1.0% to 5% by weight, relative to a total weight of the solution and having a pH from 3 to 5,
   b) pouring the chitosan solution into a mold in order to form a layer,
   c) lyophilizing the layer obtained in b) to obtain a porous layer,
   d) compressing the porous layer obtained in c) to obtain a compressed porous layer including a density of greater than or equal to 0.65 g/cm$^3$,
   e) neutralizing the compressed porous layer obtained in d) by using a $NH_4OH$ solution comprising a $NH_4OH$ concentration ranging from 0.6 to 2 mold to obtain a neutralized compressed porous layer, and,
   f) subjecting the neutralized compressed porous layer obtained in e) to one or more washing steps.

2. The method according to claim 1, wherein the chitosan solution prepared in step a) is a solution of chitosan in water having a chitosan concentration ranging from 2% to 3% by weight, relative to a total weight of the solution.

3. The method according to claim 1, wherein the chitosan includes a degree of acetylation ranging from 0 to 70%.

4. The method according to claim 1, wherein the chitosan includes a degree of acetylation ranging from 1% to 10%.

5. The method according to claim 1, wherein the chitosan includes a degree of acetylation ranging from 2% to 3%.

6. The method according to claim 1, wherein the solution includes acetic acid.

7. The method according to claim 1, wherein the pH is 3.5 by adding acetic acid.

8. The method according to claim 1, wherein the step of compressing the porous layer includes compressing the porous layer until obtaining a thickness of less than or equal to 2 mm.

9. The method according to claim 1, wherein the step of compressing the porous layer includes compressing the porous layer until obtaining a thickness of less than or equal to 0.5 mm.

10. The method according to claim 1, wherein the $NH_4OH$ solution used in step e) is a solution of $NH_4OH$ in water or ethanol.

11. The method according to claim 1, wherein the $NH_4OH$ solution used in step e) is a solution of $NH_4OH$ in ethanol including a $NH_4OH$ concentration ranging from 1 to 2 mol/l.

12. The method according to claim 1 wherein the step of neutralizing the compressed porous layer includes dipping the compressed porous layer in the $NH_4OH$ solution for a period of less than or equal to 30 minutes.

13. The method according to claim 1 wherein the step of neutralizing the compressed porous layer includes dipping the compressed porous layer in the $NH_4OH$ solution for a period ranging from 5 minutes to 20 minutes.

14. The method according to claim 1 wherein the one or more washing steps includes dipping the neutralized compressed porous layer of step e) in one or more baths of sterile water until a washing water with a pH close to 7 is obtained.

15. A method of forming an implant for reinforcing a staple zone including a chitosan based porous layer comprising the following steps:
   a) preparing a chitosan solution free of any other polymer and including a chitosan concentration ranging from 1.0% to 5% by weight, relative to the total weight of the solution,
   b) adjusting the pH of the chitosan solution to a pH ranging from 3 to 5,
   c) pouring the solution into a mold in order to form a layer,
   d) lyophilizing the layer obtained in c) to obtain a porous layer,
   e) compressing the porous layer obtained in d) to obtain a compressed porous layer including a density of greater than equal to 0.65 g/cm$^3$,
   f) neutralizing the compressed porous layer obtained in e) by using a $NH_4OH$ solution comprising a $NH_4OH$ concentration ranging from 0.6 to 2 mol/l to obtain a neutralized compressed porous layer, and,
   g) subjecting the neutralized compressed porous layer obtained in f) to one or more washing steps.

16. The method according to claim 15, wherein the chitosan solution prepared in step a) is a solution of chitosan in water having a chitosan concentration ranging from 2% to 3% by weight, relative to a total weight of the solution.

17. The method according to claim 15, wherein the chitosan includes a degree of acetylation ranging from 1% to 10%.

18. The method according to claim 15, wherein the chitosan includes a degree of acetylation ranging from 2% to 3%.

19. The method according to claim 15, wherein the pH is 3.5 by adding acetic acid.

20. The method according to claim 15, wherein the $NH_4OH$ solution used in step e) is a solution of $NH_4OH$ in water or ethanol including a $NH_4OH$ concentration ranging from 1 to 2 mol/l.

* * * * *